United States Patent [19]

Samain

[11] Patent Number: 5,570,708
[45] Date of Patent: Nov. 5, 1996

[54] PROCESS FOR THE PERMANENT RESHAPING OF KERATINOUS MATERIAL

[75] Inventor: Henri Samain, Bievres, France

[73] Assignee: L'Oreal, Paris, France

[21] Appl. No.: 419,696

[22] Filed: Apr. 11, 1995

[30] Foreign Application Priority Data

Apr. 11, 1994 [FR] France .................................. 94 04228

[51] Int. Cl.⁶ ...................................................... A45D 7/04
[52] U.S. Cl. .......................... 132/205; 132/202; 132/203; 132/204; 132/206
[58] Field of Search ..................................... 132/202, 203, 132/204, 205, 206; 8/127; 424/70.2; 427/342; 514/544

[56] References Cited

U.S. PATENT DOCUMENTS

| | | | |
|---|---|---|---|
| 2,990,832 | 7/1961 | McDonough et al. | |
| 3,533,417 | 10/1970 | Bartoszewicz | 132/204 |
| 3,860,446 | 1/1974 | Rushforth et al. | 427/342 |
| 4,066,392 | 1/1978 | Abel et al. | 8/127 |
| 4,793,993 | 12/1988 | Siuta-Mangano | 424/70.2 |
| 4,795,629 | 1/1989 | Siuta-Mangano | 514/544 |
| 4,982,750 | 1/1991 | Kaitz | |
| 5,225,191 | 7/1993 | de Labbey | 132/204 |

FOREIGN PATENT DOCUMENTS

| | | |
|---|---|---|
| 0551135 | 7/1993 | European Pat. Off. |
| 2486395 | 1/1982 | France. |
| 299882 | 9/1954 | Switzerland. |
| 373867 | 1/1964 | Switzerland. |
| 1125794 | 8/1968 | United Kingdom. |

OTHER PUBLICATIONS

Derwent Abstract of FR-A-2486395.

*Primary Examiner*—Gene Mancene
*Assistant Examiner*—Pedro Philogene
*Attorney, Agent, or Firm*—Finnegan, Henderson, Farabow, Garrett & Dunner, L.L.P.

[57] ABSTRACT

A novel treatment process for keratinous material, in particular the hair, for the purpose of obtaining a permanent reshaping of the hair, in particular in the form of permanent-waved hair, the process being characterized in that it contains the following steps: (i) applying a reducing composition to the keratinous material to be treated, which composition contains a thiol chosen from (a) cysteine, (b) cysteamine, (c) thioglycolic acid, (d) thiolactic acid, (e) 3-mercaptopropionic acid, (f) the salts of any of (a)–(e), and (g) the esters of the acids (a) and (c)–(e); a means (rollers) for placing the keratinous material under mechanical tension being used before, during or after the application of the reducing composition; optionally, the treated keratinous material is then subjected to a thermal treatment (heating); (ii) the keratinous material thus treated is then rinsed; (iii) the keratinous material thus rinsed is then left to stand; (iv) a so-called "acidic composition" is applied to the keratinous material, this composition containing at least one carboxylic acid; (v) the keratinous material thus treated is left to stand; and (vi) the keratinous material thus treated is rinsed again, the keratinous material being separated from the means for placing under tension used in step (i) either before or after application in step (iv) of the acidic composition, or before or after the rinsing of step (vi).

44 Claims, No Drawings

PROCESS FOR THE PERMANENT RESHAPING OF KERATINOUS MATERIAL

The present invention is directed to a novel treatment process for keratinous material, in particular for hair, for the purpose of obtaining a permanent reshaping of the keratinous material, in particular in the form of permanent-waved hair. The processes according to the invention can be used in the field of professional hairdressing, beauty and cosmetic salons, and the like.

It is known that the most common technique for obtaining a permanent reshaping of the hair consists, in a first step, in opening the —S—S— disulphide bridges of keratin (cystine) using a composition containing a reducing agent, i.e., a reduction step, followed, preferably after having rinsed the hair thus treated, by a second step, in reforming the disulphide bridges by applying, to the hair which has been placed beforehand under tension, i.e., by curlers or the like, an oxidizing composition, i.e., an oxidation step, also referred to as fixing, so as finally to give the desired shape to the hair. This technique thus makes it possible to achieve either the waving of the hair or the decurling or straightening thereof. The new shape given to the hair by a chemical treatment such as that described above is eminently durable over time and in particular, resists the action of washing with water or with shampoos; this is in contrast to the simple standard techniques for temporary reshaping, such as curling.

The reducing compositions which may be used in order to carry out the first step of a permanent-waving operation generally contain, as reducing agents, sulphites, bisulphites or thiols. Among the thiols, there may be mentioned cysteine and the various derivatives thereof, cysteamine and the derivatives thereof, thiolactic acid, thioglycolic acid and the esters thereof, especially glyceryl monothioglycolate and thioglycerol. In this regard, and although it possesses an unpleasant odor, thioglycolic acid is particularly effective and thus constitutes the reference compound in permanent-waving for reducing the disulphide bridges in keratin. With regard to cysteine, which produces a much weaker odor than that of thioglycolic acid or of glyceryl monothioglycolate, the degree of curling obtained is unfortunately less and far from being totally satisfactory.

As regards the oxidizing compositions required to carry out the fixing step, use is usually made, in practice, of compositions based on aqueous hydrogen peroxide solution or on alkali metal bromates, these oxidizing agents generally being used in concentrations greater than 0.8N. However, it turns out that the use of such oxidizing agents at such concentrations has the drawback in particular of leading to a more or less pronounced degradation of the original color of the hair.

In addition, and in particular in the case where the reducing agent used is thioglycolic acid, it is observed that the succession of reduction-oxidation cycles (i.e. of permanent-waving operations) on the hair leads, in a harmful way, to a gradual degradation not only of the color of the hair (bleaching) but also of its mechanical strength (lowering of the breaking energy) in particular due to a significant increase in the level of keratocysteic acid in the hair treated.

The object of the present invention is especially to overcome the above problems.

Specifically, an object of the present invention is to provide a novel treatment process which is suitable for the permanent reshaping of keratinous material and which makes it possible to do away with the use of conventional fixing steps using powerful oxidizing agents in large amounts.

An object of the invention is also to provide a process such as that described above which makes it additionally possible to obtain high quality curls with good hold.

Another object of the invention is to provide a process such as that described above which makes it possible to limit, or even to prevent altogether, the mechanical degradation of the hair, after repetition of the treatment.

An additional object of the invention is to provide a process such as that described above, which limits, or which even prevents altogether, the bleaching of the hair.

A further object of the invention is to provide a process such as that described above which is, overall, largely odorless, on the one hand, and largely nonirritating to the skin and/or the scalp, on the other hand.

It has been discovered that these objects, and others, could be achieved successfully by making a suitable choice of the so-called starting reducing composition combined with a specific procedure for using this composition. This discovery forms the basis of the present invention.

Thus, the present invention provides a novel treatment process which is suitable for the reshaping and/or styling, in a permanent manner, of keratinous material, and in particular of the hair, which process comprises the following steps: (i) applying to keratinous material a reducing composition containing at least one thiol selected from (a) cysteine, (b) cysteamine, (c) thio-glycolic acid, (d) thiolactic acid, (e) 3-mercaptopropionic acid, (f) the salts of any of (a)–(e), and (g) the esters of any of the acids (a) and (c)–(e); the keratinous material being placed under mechanical tension, e.g., by rollers, curlers and the like, before, during or after the composition is applied to the keratinous material; (ii) rinsing the keratinous material to which the composition has been applied; (iii) allowing the rinsed keratinous material to undergo a waiting phase; (iv) subsequently applying an acidic composition containing at least one carboxylic acid to the keratinous material of (iii); (v) allowing the keratinous material treated in (iv) to undergo a second waiting phase; (vi) rinsing the keratinous material of (v); wherein the keratinous material is separated from the mechanical tension of step (i) either before or after the application of the acidic composition in step (iv) or before or after the rinsing in step (vi).

The present invention also includes a process such as that described above, wherein prior to the rinsing of the keratinous material in step (ii), the keratinous material to which the reducing composition has been applied is subjected to a thermal treatment.

The process according to the invention is particularly suitable for obtaining permanent-waved hair.

When applied to healthy hair, and even when repeated several times, the process according to the invention has the main advantages, among others, of giving, without the release of unpleasant odors, on the one hand, and in a manner which is non-irritating to the skin and/or the scalp, on the other hand, non-bleached or substantially non-bleached hair which is mechanically strong and has beautiful curls.

However, other characteristics, aspects and advantages of the invention will emerge even more clearly on reading the detailed description which will follow, as well as the various concrete, but in no way limiting, examples intended to illustrate the invention.

Although the account which follows is centered essentially on the specific case of the treatment of the hair, it is noted that the process according to the invention may be applied to any keratinous material in general, in particular eyelashes, moustaches, hairs, wool, and the like.

The reducing agents used within the context of the process according to the invention are cysteine, cysteamine, thioglycolic acid, thiolactic acid, 3-mercaptopropionic acid, the salts thereof and the esters of these acids.

Among the acceptable cysteine and cysteamine salts which may preferably be mentioned are the hydrochlorides, hydrobromides, citrates, acetates and sulphates.

Among the acceptable thioglycolic acid, thiolactic acid and 3-mercaptopropionic acid salts which may preferably be mentioned are the ammonium salts, the primary, secondary or tertiary amine salts, and the alkaline-earth metal salts. Primary, secondary or tertiary amine salts which may preferably be mentioned are monoethanolamine, diisopropanolamine and triethanolamine.

Preferred esters of the acids which may be mentioned are glyceryl monothioglycolate, ethylene glycol monothioglycolate, the azeotropic mixture of 2-hydroxypropyl thioglycolate and 2-hydroxy-1-methyl-ethyl thioglycolate described in Patent Application FR-A-2 679 448, the disclosure of which is incorporated herein by reference, glyceryl monothiolactate, ethylene glycol monothiolactate, glyceryl 3-mercaptopropionate and ethylene glycol 3-mercaptopropionate.

These reducing agents are preferably used in cosmetically acceptable compositions, which are, moreover, already well known per se in the existing state of the art for curling formulations intended to perform the first step (reduction) of a permanent-waving operation. Thus, as common and conventional additives, which may be used alone or as mixtures, there may more preferably be mentioned nonionic, anionic, cationic or amphoteric surface-active agents, and among these, there may preferably be mentioned alkyl sulphates, alkylbenzene sulphates, alkyl ether sulphates, alkyl sulphonates, quaternary ammonium salts, alkylbetaines, oxyethylenated alkylphenols, fatty acid alkanolamides, oxyethylenated fatty acid esters and other nonionic surfactants of the hydroxypropyl ether type.

When the reducing composition contains at least one surface-active agent, the surface-active agent is preferably present at a maximum concentration of 30% by weight, and more preferably ranges from 0.5 to 10% by weight, relative to the total weight of the reducing composition.

In the aim of enhancing the cosmetic properties of the hair or alternatively of attenuating or preventing the degradation thereof, the reducing composition may also contain a treating agent of cationic, anionic, nonionic or amphoteric nature.

Among the particularly preferred treating agents, there may be mentioned those described in French Patent Applications Nos. 2,598,613 and 2,470,596, the disclosures of which are incorporated herein by reference. It is also possible to use as treating agents linear or cyclic, volatile or non-volatile silicones and mixtures thereof, polydimethylsiloxanes, quaternized polyorganosiloxanes such as those described in French Patent Application No. 2,535,730, the disclosure of which is incorporated herein by reference, polyorganosiloxanes having aminoalkyl groups modified with alkoxycarbonylalkyl groups such as those described in U.S. Pat. No. 4,749,732, the disclosure of which is incorporated herein by reference, polyorganosiloxanes such as the polydimethylsiloxane/polyoxyalkyl copolymer of the Dimethicone Copolyol type, a polydimethylsiloxane having terminal stearoxy-groups (stearoxydi-methicone), a poty-dimethylsiloxane/dialkylammonium acetate copolymer or a polydimethylsiloxane poly-alkylbetaine copolymer which are described in British Patent Application No. 2,197,352, the disclosure of which is incorporated herein by reference, polysiloxanes organically modified with mercapto or mercaptoalkyl groups such as those described in French Patent No. 1,530,369 and in European Patent Application No. 295,780, the disclosures of which are incorporated herein by reference, and silanes such as stearoxytrimethyl-silane.

The reducing composition may also contain other treating ingredients such as cationic polymers such as those used in the compositions of French Patents Nos. 79,32078 (PR-A-2,472,382) and 80,26421 (FR-A-2,495,931), the disclosures of which are incorporated herein by reference, or alternatively cationic polymers of the ionone type such as those used in the compositions of the Luxembourg Patent No. 83703, the disclosure of which is incorporated herein by reference, basic amino acids (such as lysine and arginine) or acidic amino acids (such as glutamic acid and aspartic acid), peptides and derivatives thereof, protein hydrolysates, waxes, swelling agents and penetrating agents or agents making it possible to reinforce the effectiveness of the reducing agent such as the $SiO_2$/PDMS (polydimethylsiloxane) mixture, dimethylisosorbitol, urea and derivatives thereof, pyrrolidone, N-alkylpyrrolidones, thiamorpholinone, alkyl ethers of alkyleneglycol or of dialkyleneglycol such as, for example, propylene glycol monomethyl ether, dipropylene glycol monomethyl ether, ethylene glycol monoethyl ether and diethylene glycol monoethyl ether, $C_3$–$C_6$ alkanediols such as, for example, 1,2-propanediol and 1,2-butanediol, 2-imidazolidinone, and other compounds such as fatty alcohols, lanolin derivatives, active ingredients such as pantothenic acid, agents for combating hair loss, anti-dandruff agents, thickeners, suspension agents, sequestering agents, opacifying agents, dyes and sunscreen agents, as well as fragrances and preserving agents.

When cysteine or one of the salts thereof is used as a reducing agent, the pH of the reducing composition preferably ranges from 7.5 to 11.5, and more preferably from 9 to 10.

When cysteamine or one of the salts thereof is used as a reducing agent, the pH of the reducing composition preferably ranges from 7 to 11, and more preferably from 8 to 9.

When thioglycolic acid, thiolactic acid, or 3-mercaptopropionic acid, or one of the salts thereof, is used as a reducing agent, the pH of the whole reducing composition preferably ranges from 6.5 to 11.5, and even more preferably ranges from 7 to 10.

When the esters of thioglycolic acid, of thiolactic acid, or of 3-mercaptopropionic acid are used as a reducing agent, the pH of the whole reducing composition preferably ranges from 5 to 11, and even more preferably ranges from 6 to 10.

These pHs may be obtained and/or adjusted conventionally either by addition of basifying agents, for example such as aqueous ammonia, monoethanolamine, diethanolamine, triethanolamine, isopropanolamine, diisopropanolamine, 1,3-propanediamine, an ammonium or alkali metal carbonate or bicarbonate, an organic carbonate such as guanidine carbonate, or alternatively by an alkali metal hydroxide; it obviously being possible for all of these compounds to be taken alone or as a mixture. The pH may also be obtained and/or adjusted by the addition of acidifying agents, for example such as hydrochloric acid, acetic acid, lactic acid or boric acid.

In the permanent-waving reducing compositions which may be used within the context of the invention, the reducing agents mentioned above are present at a concentration which may preferably range from 1 to 30% by weight, and more preferably from 3 to 20% by weight, relative to the total weight of the reducing composition.

The reducing composition may be in the form of a lotion, which may or may not be thickened, a cream, a gel or any other suitable form.

The reducing composition may also be of the exothermic type, that is to say, that it causes a certain heating-up upon application to the hair, this providing a certain pleasantness to the person undergoing the permanent-waving or the hair straightening.

The reducing composition may also contain a solvent such as, for example, ethanol, propanol or isopropanol or glycerol at a preferred maximum concentration of 20% relative to the total weight of the composition.

The vehicle for the compositions is preferably water or an aqueous-alcoholic solution of a lower alcohol such as ethanol, isopropanol or butanol.

When the compositions of the invention are intended for use in an operation of decurling or straightening of the hair, the reducing composition is preferably in the form of a thickened cream so as to keep the hair as straight as possible. These creams are prepared in the form of "heavy" emulsions, for example based on glyceryl stearate, glycol stearate, auto-emulsifiable waxes, fatty alcohols, and the like.

It is also possible to use liquids or gels containing thickening agents such as carboxyvinyl copolymers or polymers which "stick" the hair together and keep it in the smooth position during the exposure time.

Finally, the compositions may also be in the so-called "auto-neutralizing" or alternatively "auto-regulated" form and, in which case, the reducing agents used according to the invention are combined with at least one disulphide known for its use in a reducing composition for an auto-neutralizing permanent-waving.

Among such known disulphides which may preferably be mentioned are dithioglycclic acid, dithioglycerol, cysteamine, N,N'-diacetylcysteamine, cystine, pantethine, and the disulphides of the N-(mercaptoalkyl)-ω-hydroxyalkyl amides described in Patent Application EP-A-354,835, the disclosure of which is incorporated herein by reference, the disulphides of the N-mono- or N,N-dialkylmercapto-4-butyramides described in Patent Application EP-A-368,763, the disclosure of which is incorporated herein by reference, the disulphides of the aminomercapto-alkylamides described in Patent Application EP-A-432,000, the disclosure of which is incorporated herein by reference, the disulphides of N-(mercaptoalkyl)succinamic acid derivatives or of N-(mercaptoalkyl)succinimide acid derivatives described in Patent Application EP-A-465,342, the disclosure of which is incorporated herein by reference, and the disulphides of alkylaminomercaptoalkylamides described in Patent Application EP-A-514,282, the disclosure of which is incorporated herein by reference. These disulphides are preferably present in a molar ratio ranging from 0.5 to 2.5, and more preferably from 1 to 2, relative to the reducing agent (see U.S. Pat. No. 3,768,490, the disclosure of which is incorporated herein by reference).

In accordance with the first step of the process according to the present invention (step (i)), the compositions containing the reducing agent or agents according to the invention are applied to the hair to be treated, which will preferably have been moistened beforehand.

This application may be performed before, during or after the usual step of placing the hair under tension in a shape corresponding to the final shape desired for the hair, curls for example; it being possible for this step itself to be carried out by any means, preferably mechanical means, which is suitable and known per se for maintaining the hair under tension, for example such as rollers, curlers and the like.

According to an optional step of the process of the invention, it is possible, after application of the reducing composition in step (i), to allow the hair to undergo a thermal treatment, that is to say to a heating. In this case, the heating temperature preferably ranges from 30° to 60° C. Although not obligatory, this heating is nevertheless preferred, since it enables the final degree of curliness of the hair to be adjusted at will. Obviously, it is possible to work at room temperature, and this is therefore not excluded from the scope of the invention. In practice, this operation may be carried out using a hairstyling hood, a hair dryer, an infrared radiation dispenser or any other conventional heating apparatus.

Before performing the rinsing of step (ii) which follows therefrom, it is conventionally convenient and preferable to allow the hair to which the reducing composition has been applied to rest in a waiting phase for a few minutes, preferably for from 2 to 30 minutes, and more preferably for from 5 to 20 minutes, so as to allow good time for the reducing agent to act fully on the hair. During this waiting phase, which can be integrated with the optional heating step mentioned above, care is taken that the hair does not become completely dry and thus remains damp until the next step is carried out (possible use of bonnets or protective gels for example).

In a second essential step of the process according to the invention (step (ii)), the hair impregnated with reducing composition is rinsed carefully, generally with water.

According to a third essential step of the treatment process according to the invention (step/iii)), the hair rinsed in step (ii) is allowed to rest in a standing or waiting phase. According to the invention, this waiting phase for the rinsed hair may preferably last for a period ranging from 3 to 60 minutes, and more preferably lasts for a period ranging from 5 to 30 minutes. This step is preferably carried out by leaving the moistened hair after the rinsing operation to rest in the open air (room temperature). A waiting phase carried out at a higher temperature is not excluded, and is equally suitable; it may be carried out until the keratinous material is totally dry. The hair may be rinsed again after this waiting phase.

In the process according to the invention, when the reducing composition contains thioglycolic acid, thiolactic acid or 3-mercaptopropionic acid, or salts thereof at a concentration above 8% by weight relative to the total weight of the composition, the pH of the reducing composition is preferably less than 9 and the waiting phase of step (iii) is preferably less than 7 minutes.

According to a fourth essential step of the treatment process according to the invention (step (iv)), a so-called "acidic composition" is applied to the keratinous material, this composition containing at least one carboxylic acid. The keratinous material may be separated, before or after the application of the acidic composition, from the means for placing the keratinous material under tension used in step (i).

Preferred carboxylic acids include simple carboxylic acids, polycarboxylic acids and (poly)hydroxy(poly)carboxylic acids, which may, of course, be taken alone or as a mixture.

As carboxylic acids which may be used in the compositions according to the invention, there may more preferably be mentioned lactic acid, tartaric acid, acetic acid, glycolic acid and citric acid.

According to a particularly preferred embodiment of the process of the present invention, the acid used is citric acid.

The concentration of carboxylic acid in the so-called acidic composition preferably ranges from 0.2% to 40% by weight relative to the total weight of the acidic composition, and more preferably ranges from 1 to 20% by weight. The pH of the so-called acidic composition preferably ranges from 1.8 to 7.5 and may be adjusted using an alkaline agent chosen from aqueous ammonia, monoethanolamine, diethanolamine, triethanolamine, 1,3-propanediamine, ammonium carbamate, an ammonium or alkali metal carbonate or bicarbonate, an organic carbonate or an alkali metal hydroxide. Depending on the pH of the so-called acidic composition, the carboxylic acid present may be free as an acid or bound as a salt.

Since lasting odors may develop on the hair after such a treatment, it has been discovered that these odors can be attenuated, or even removed altogether, by applying, according to the present process, an acidic composition containing, besides the carboxylic acid, an oxidizing agent in a very low amount.

The acidic composition may thus contain at least one oxidizing agent at a concentration which preferably ranges from $5 \times 10^{-5}$ to 0.17N (Normal), and more preferably ranges from $1 \times 10^{-4}$ to 0.17N. The oxidizing agent is preferably chosen from aqueous hydrogen peroxide solution, alkali metal bromates, persalts, polythionates, chloramine T, N-bromosuccinimide, N-chlorosuccinimide and halogenated hydantoin derivatives. Since the oxidizing agent is used at a very low concentration, the step of application of the acidic composition cannot be considered a fixing step.

The acidic composition may also contain cosmetic adjuvants such as those mentioned above for the reducing composition. The acidic composition may be in the form of a lotion, which may or may not be thickened, a cream, a gel, a shampoo, a conditioner or any other suitable form.

When the acidic composition is applied to the hair before separating it from the means for placing under tension, the hair may be left to stand or rest for a few minutes, for example 5 minutes, followed by removal of the hair from the mechanical means which held the hair under tension and in the desired shape during the treatment.

In another variant of the process, it is possible to separate the hair from the means for placing under tension and then to apply the acidic composition to the hair and to massage the hair in order to promote impregnation of the acidic composition in the hair.

In a fifth essential step of the process according to the invention (step (v)), the hair treated in step (iv) is allowed to undergo a waiting phase. According to the invention, this waiting phase of the treated hair preferably lasts for a period ranging from 10 seconds to 30 minutes, and more preferably lasts for a period ranging from 1 to 15 minutes.

Finally, in the last step of the process according to the invention (step (vi)), the hair impregnated with the acidic composition is rinsed carefully, generally with water. It is possible, before or after the rinsing, to separate the keratinous material from the tension means used in step (i) if this operation has not been carried out before or after the application of the acidic composition.

Hair of beautiful curliness, the curls being tonic, is obtained, without it having been necessary to use a chemical fixing step (oxidation).

The subject of the invention is also a multi-compartment device or "kit", which comprises, in a first compartment, a reducing composition as defined above and, in a second compartment, a so-called acidic composition as defined above, the device being produced for the purpose of carrying out the process according to the invention.

Concrete examples illustrating the invention will now be given. For the purposes of a significant comparison, the same starting hair (before treatment) was used for all the examples.

EXAMPLE 1 (INVENTION)

A reducing composition having the following characteristics was used:

| thioglycolic acid | 9 g |
|---|---|
| aqueous ammonia | qs pH 7 |
| ammonium carbonate | 2 g |
| monoethanolamine | qs pH 8.5 |
| demineralized water | qs 100 g | and an acidic composition having the following characteristics was used:

| citric acid | 10 g |
|---|---|
| aqueous ammonia | qs pH 4.5 |
| chloramine T | 0.2 g or 0.014N (Normal) |
| demineralized water | qs 100 g |

The procedure was as follows: the above reducing composition was applied to a lock of damp and rollered hair (diameter of the rollers: 9 mm). A plastic bonnet was then placed over the lock (thereby making it possible to prevent drying of the hair during the following heating step) which was then installed under a hood (45° C.) for 15 minutes. The bonnet was then removed and the lock was rinsed thoroughly and carefully with water. The lock was returned under the hood (45° C.) for 15 minutes and then rinsed again with water. The above acidic composition was then applied and was left to stand for 5 minutes at room temperature. The lock was then rinsed thoroughly with water and the roller was removed (de-rollering).

A lock having beautiful curliness was finally obtained. After combing through, the hair rapidly resumed its curled shape and had little odor.

EXAMPLE 2 (COMPARATIVE)

A permanent reshaping process was performed using a fixing step.

A fixing (oxidizing) composition having the following characteristics was used:

| aqueous hydrogen peroxide solution at a concentration of 35% by weight | 7 g or 1.44N |
|---|---|
| citric acid | qs pH 3 |
| demineralized water | qs 100 g |

The procedure was as follows: the reducing composition of Example 1 was applied to a lock of damp and rollered hair (diameter of the rollers: 9 mm). A plastic bonnet was then placed over the lock which was then installed under a hood (45° C.) for 15 minutes. The bonnet was then removed and the lock was rinsed thoroughly and carefully with water. The above fixing composition was then applied and was left to stand for 10 minutes. The lock was finally rinsed thoroughly with water and the rollers were removed.

The operation was performed three times in succession.

EXAMPLE 3 (INVENTION)

The process of Example 1 was carried out three times in succession.

The gain in keratocysteic acid of the treated locks of Examples 2 and 3 was determined by analysis of the amino acids.

It was observed that the lock of Example 2 had a gain in keratocysteic acid of +0.9% whereas the lock of Example 3 according to the invention had a gain in keratocysteic acid of +0.1%, that is to say a much lower gain than that of Example 2.

EXAMPLE 4 (INVENTION)

The reducing composition of Example 1 was applied to a lock of damp and rollered hair (diameter of the rollers: 9 mm). A plastic bonnet was then placed over the lock (thereby making it possible to prevent drying of the hair during the following heating step) which was then installed under a hood (45° C.) for 10 minutes. The bonnet was then removed and the lock was rinsed thoroughly and carefully with water. The lock was returned under the hood (45° C.) for 10 minutes and then rinsed again with water. The acidic composition of Example 1 was then applied and was left to stand for 5 minutes at room temperature. The lock was then rinsed thoroughly with water and the roller was removed (de-rollering).

A lock having beautiful curliness was finally obtained. After combing through, the hair rapidly resumed its curled shape and had little odor.

EXAMPLE 5 (INVENTION)

The reducing composition of Example 1 was applied to a lock of damp and rollered hair (diameter of the rollers: 9 mm). A plastic bonnet was then placed over the lock (thereby making it possible to prevent drying of the hair during the following heating step) which was then installed under a hood (45° C.) for 15 minutes. The bonnet was then removed and the lock was rinsed thoroughly and carefully with water. The lock was returned under the hood (45° C.) for 15 minutes and then rinsed again with water. The acidic composition of Example 1 was then applied and was left to stand for 2 minutes at room temperature. The roller was then removed (de-rollering). The lock of hair was massaged, left to stand for 3 minutes, and was rinsed thoroughly with water.

A lock having beautiful curliness was finally obtained. After combing through, the hair rapidly resumes its curled shape and had little odor.

EXAMPLE 6 (INVENTION)

The reducing composition of Example 1 was applied to a lock of damp and rollered hair (diameter of the rollers: 9 mm). A plastic bonnet was then placed over the lock which was then installed under a hood (45° C.) for 15 minutes. The bonnet was then removed and the lock was rinsed thoroughly and carefully with water. The lock was returned under the hood (45° C.) for 15 minutes and then rinsed again with water. The roller was removed (de-rollering), the acidic composition of Example 1 was applied, and the lock of hair was massaged. It was left to stand for 5 minutes at room temperature and was rinsed thoroughly with water.

A lock having beautiful curliness was finally obtained. After combing through, the hair rapidly resumed its curled shape and had little odor.

EXAMPLE 7 (INVENTION)

A reducing composition having the following characteristics was used:

| | |
|---|---|
| thioglycolic acid | 11 g |
| 3-mercaptopropionic acid | 4 g |
| aqueous ammonia | qs pH 7 |
| ammonium carbonate | 2 g |
| monoethanolamine | qs pH 8.5 |
| demineralized water | qs 100 g | and an acidic composition having the following characteristics was used:

| | |
|---|---|
| citric acid | 10 g |
| aqueous ammonia | qs pH 4.5 |
| aqueous hydrogen peroxide peroxide solution at a concentration of 35% by weight | 0.5 g or 0.1N |
| demineralized water | qs 100 g |

The procedure was that of Example 4.

A lock having beautiful curliness was finally obtained. After combing through, the hair rapidly resumed its curled shape and had little odor.

EXAMPLE 8 (INVENTION)

A reducing composition having the following characteristics was used:

| | |
|---|---|
| cysteine | 11 g |
| monoethanolamine | qs pH 9.5 |
| demineralized water | qs 100 g | and an acidic composition having the following characteristics was used:

| | |
|---|---|
| glycolic acid | 8 g |
| aqueous ammonia | qs pH 4 |
| aqueous hydrogen peroxide solution at a concentration of 35% by weight | 0.5 g or 0.1N |
| demineralized water | qs 100 g |

The procedure was that of Example 1.

A lock having beautiful curliness was finally obtained. After combing through, the hair rapidly resumed its curled shape and had little odor.

EXAMPLE 9 (INVENTION)

The reducing composition of Example 8 was applied to a lock of damp and rollered hair (diameter of the rollers: 9 mm). A plastic bonnet was then placed over the lock which was then installed under a hood (45° C.) for 30 minutes. The bonnet was then removed and the lock was rinsed thoroughly and carefully with water. The acidic composition of Example 1 was then applied and the lock was left to stand for 5 minutes at room temperature. It was then rinsed thoroughly with water and the roller was removed (de-rollering).

A lock having beautiful curliness was finally obtained. After combing through, the hair rapidly resumed its curled shape and had little odor.

EXAMPLE 10 (INVENTION)

An acidic composition in the form of a shampoo having the following characteristics was used:

| | |
|---|---|
| citric acid | 8 g |
| aqueous ammonia | qs pH 4.5 |
| sodium lauryl ether sulphate | 0.3 g AM |
| chloramine T | 0.12 g or 0.0084N |
| demineralized water | qs 100 g |

The procedure was as follows: the reducing composition of Example 1 was applied to a lock of damp and rollered hair (diameter of the rollers: 9 mm). A plastic bonnet was then placed over the lock which was then installed under a hood (45° C.) for 15 minutes. The bonnet was then removed and the lock was rinsed thoroughly and carefully with water. The lock was returned under the hood (45° C.) for 15 minutes and then rinsed again with water. The roller was removed (de-rollering), the above acidic composition was applied and the lock of hair was massaged as in the context of a shampoo, for 3 minutes. It was rinsed thoroughly with water.

A lock having beautiful curliness was finally obtained. After combing through, the hair rapidly resumed its curled shape and had little odor.

EXAMPLE 11 (INVENTION)

An acidic composition in the form of a shampoo having the following characteristics was used:

| | |
|---|---|
| citric acid | 8 g |
| aqueous ammonia | qs pH 4.5 |
| sodium lauryl ether sulphate | 0.4 g AM |
| tegobetaine | 0.4 g AM |
| aqueous hydrogen peroxide solution at a concentration of 35% by weight | 0.7 g or 0.14N |
| demineralized water | qs 100 g |

The procedure was as follows: the reducing composition of Example 1 was applied to a lock of damp and rollered hair (diameter of the rollers: 9 mm). A plastic bonnet was then placed over the lock which was then installed under a hood (45° C.) for 15 minutes. The bonnet was then removed and the lock was rinsed thoroughly and carefully with water. The lock was returned under the hood (45° C.) for 15 minutes and then rinsed again with water. The above acidic composition was applied and left to stand for 4 minutes, and the rollers were removed de-rollering). The lock of hair was then massaged as in the context of a shampoo, for 3 minutes, followed by rinsing thoroughly with water.

A lock having beautiful curliness was finally obtained. After combing through, the hair rapidly resumed its curled shape and had little odor.

EXAMPLE 12 (INVENTION)

An acidic composition having the following characteristics was used:

| | |
|---|---|
| citric acid | 10 g |
| aqueous ammonia | qs pH 4.5 |
| sodium lauryl ether sulphate | 0.4 g AM |
| demineralized water | qs 100 g |

The procedure was as follows: the reducing composition of Example 7 was applied to the pre-rollered hair (diameter of the rollers: 9 mm) of a Japanese woman. A plastic bonnet was then placed over the hair which was left in place under a hood (45° C.) for 15 minutes. The bonnet was removed, the hair was rinsed and the bonnet was replaced and left in place under the hood (45° C.) for 15 minutes. The hair was rinsed again and the above acidic composition was then applied. It was left in place for 4 minutes at room temperature and the hair was rinsed. The rollers were removed.

Beautiful curliness was finally obtained. After combing through, the hair resumed a curled shape and had little odor.

What is claimed is:

1. A treatment process for the permanent reshaping of keratinous material, which comprises the following steps:
   (i) applying to keratinous material a reducing composition containing at least one thiol selected from (a) cysteisa, (b) cystonline, (c) thioglycolic acid, (d) thiolactic acid, (e) 3-mercaptopropionic acid, (f) the salts of any of (a)–(e), and (g) the esters of any of the acids (a) and (c)–(e); said keratinous material being placed under mechanical tension before, during or after said composition is applied to said keratinous material;
   (ii) rinsing said keratinous material to which said composition has been applied;
   (iii) allowing the rinsed keratinous material to undergo a waiting phase;
   (iv) subsequently applying an acidic composition containing at least one carboxylic acid to the keratinous material of (iii);
   (v) allowing the keratinous material treated in (iv) to undergo a second waiting phase; and
   (vi) rinsing the keratinous material of (v); wherein said keratinous material is separated from said mechanical tension of step (i) either before or after said application of said acidic composition in step (iv) or before or after said rinsing in step (vi).

2. A process according to claim 1, wherein prior to said rinsing of said keratinous material in step (ii), the keratinous material to which said composition has been applied is subjected to a thermal treatment.

3. A process according to claim 1, wherein said at least one thiol is selected from cysteine and one of its salts, and further wherein the pH of said reducing composition ranges from 7.5 to 11.5.

4. A process according to claim 3, wherein said pH ranges from 9 to 10.

5. A process according to claim 1, wherein said at least one thiol is selected from cysteamine and one of its salts, and further wherein the pH of said reducing composition ranges from 7 to 11.

6. A process according to claim 5, wherein said pH ranges from 8 to 9.

7. A process according to claim 1, wherein said at least one thiol is selected from thioglycolic acid, thiolactic acid, 3-mercaptopropionic acid, and one of their salts, and further wherein the pH of said reducing composition ranges from 6 to 11.5.

8. A process according to claim 7, wherein said pH ranges from 7 to 10.

9. A process according to claim 1, wherein said at least one thiol is selected from an ester of thioglycolic acid, an ester of thiolactic acid, and an ester of 3-mercaptopropionic acid, and further wherein the pH of said reducing composition ranges from 5 to 11.

10. A process according to claim 9, wherein said pH ranges from 6 to 10.

11. A process according to claim 1, wherein said at least one thiol is selected from cysteine, cysteamine, and the hydrochloride, hydrobromide, citrate, acetate, and sulphate salts of cysteine and cysteamine.

12. A process according to claim 1, wherein said at least one thiol is selected from thioglycolic acid, thiolactic acid, 3-mercaptopropionic acid, and the ammonium, secondary or tertiary amine and alkaline-earth metal salts of any of thioglycoiic acid, thiolactic acid, and 3-mercaptopropionic acid.

13. A process according to claim 1, wherein said at least one thiol is present in said reducing composition in an amount ranging from 1 to 30% by weight relative to the total weight of the reducing composition.

14. A process according to claim 13, wherein said at least one thiol is present in an amount ranging from 3 to 20% by weight relative to the total weight of the reducing composition.

15. A process according to claim 1, wherein prior to the application in step (i) of the reducing composition to the keratinous material, the keratinous material is moistened.

16. A process according to claim 2, wherein said thermal treatment is carried out at a temperature ranging from 30° to 60° C.

17. A process according to claim 2, wherein before carrying out the rinsing operation of step (ii), the keratinous material of step (i) is allowed to rest in a waiting phase, during which the keratinous material is subjected to said thermal treatment.

18. A process according to claim 17, wherein said waiting phase lasts for a period ranging from 2 to 30 minutes.

19. A process according to claim 18, wherein said waiting phase lasts for a period ranging from 5 to 20 minutes.

20. A process according to claim 1, wherein heating occurs during the waiting phase of step (iii).

21. A process according to claim 1, wherein said waiting phase of step (iii) lasts for a period ranging from 3 to 60 minutes.

22. A process according to claim 21, wherein said waiting phase lasts for a period ranging from 5 to 30 minutes.

23. A process according to claim 1, wherein said waiting phase of step (iii) is carried out until the rinsed keratinous material is completely dried.

24. A process according to claim 1, wherein an additional rinsing operation is carried out following step (iii).

25. A process according to claim 1, wherein said at least one carboxylic acid is selected from simple carboxylic acids, polycarboxylic acids, and (poly)hydroxy(poly)carboxylic acids.

26. A process according to claim 25, wherein said at least one carboxylic acid is selected from lactic acid, tartaric acid, acetic acid, glycolic acid and citric acid.

27. A process according to claim 26, wherein said at least one carboxylic acid is citric acid.

28. A process according to claim 25, wherein the concentration of said at least one carboxylic acid in said acidic composition ranges from 0.2% to 40% by weight relative to the total weight of said acidic composition.

29. A process according to claim 28, wherein the concentration of said at least one carboxylic acid in said acidic composition ranges from 1 to 20% by weight relative to the total weight of said acidic composition.

30. A process according to claim 25, wherein the pH of said acidic composition ranges from 1.8 to 7.5.

31. A process according to claim 30, wherein said pH is obtained or adjusted using an alkaline agent selected from aqueous ammonia, mono-ethanolamine, diethanolamine, triethanolamine, 1,3-propanediamine, ammonium carbamate, an ammonium or alkali metal carbonate or bicarbonate, an organic carbonate and an alkali metal hydroxide.

32. A process according to claim 1, wherein said acidic composition contains an oxidizing agent in a concentration ranging from $5\times10^{-5}$ to 0.17N.

33. A process according to claim 32, wherein said acidic composition contains an oxidizing agent in a concentration ranging from $1\times10^{-4}$ to 0.17N.

34. A process according to claim 32, wherein said oxidizing agent is selected from aqueous hydrogen peroxide solution, alkali metal bromates, persalts, polythionates, chloramine T, N-bromosuccinimide, N-chlorosuccinimide and halogenated hydantoin derivatives.

35. A process according to claim 1, wherein said reducing composition and said acidic composition additionally contain cosmetically acceptable adjuvants.

36. A process according to claim 35, wherein said cosmetically acceptable adjuvants are selected from nonionic, anionic, cationic or amphoteric surface active agents, treating agents, active ingredients, agents for combating hair loss, anti-dandruff agents, thickeners, suspension agents, sequestering agents, opacifying agents, dyes, sunscreen agents, fragrances and preserving agents.

37. A process according to claim 1, wherein said reducing composition and said acidic composition are, independently of each other, in the form of a lotion, which may or may not be thickened, a cream or a gel.

38. A process according to claim 1, wherein said acidic composition is in the form of a shampoo or a conditioner.

39. A process according to claim 1, wherein said waiting phase of step (iii) lasts for a period ranging from 10 seconds to 30 minutes.

40. A process according to claim 39, wherein said waiting phase of step (iii) lasts for a period ranging from 1 to 15 minutes.

41. A process according to claim 1, wherein said keratinous material comprises hair.

42. A kit for the permanent reshaping of keratinous material comprising at least two compartments, wherein a first compartment comprises a reducing composition containing at least one thiol selected from (a) cysteine, (b) cysteamine, (c) thioglycolic acid, (d) thiolactic acid, (e) 3-mercaptopropionic acid, (f) the salts of any of (a)–(e), and (g) the esters of any of the acids (a) and (c)–(e), and wherein a second compartment comprises an acidic composition containing at least one carboxylic acid.

43. A process according to claim 1, wherein said composition is in auto-neutralizing or auto-regulating form.

44. A process according to claim 1, wherein said reducing composition contains thioglycolic acid or a salt thereof, thiolactic acid or a salt thereof, or 3-mercaptopropionic acid or a salt thereof at a concentration of at least 8% by weight relative to the total weight of the composition, wherein the pH of said composition is less than 9, and further wherein the waiting phase of step (iii) lasts for a period of less than 7 minutes.

\* \* \* \* \*

UNITED STATES PATENT AND TRADEMARK OFFICE
CERTIFICATE OF CORRECTION

PATENT NO.: 5,570,708

DATED: November 5, 1996

INVENTOR(S): Henri SAMAIN

It is certified that an error appears in the above-identified patent and that said Letters Patent is hereby corrected as shown below:

In the Abstract:

lines 10-11, delete "a means (rollers) for"; and lines 21-22, delete "means for placing under" and insert therefor --mechanical--.

Claim 1, col. 12, lines 17-18, "(a) cysteisa, (b) cystonline," should read --(a) cysteine, (b) cysteamine--; and Claim 12, col. 13, line 9, "thioglycoiic" should read --thioglycolic--.

Signed and Sealed this

Twenty-fourth Day of June, 1997

Attest:

BRUCE LEHMAN

Attesting Officer

Commissioner of Patents and Trademarks